US00PP28926P2

(12) United States Plant Patent
Horvath

(10) Patent No.: US PP28,926 P2
(45) Date of Patent: Jan. 30, 2018

(54) ***SEDUM ELLACOMBIANUM* PLANT NAMED 'CUTTING EDGE'**

(50) Latin Name: *Sedum ellacombianum*
Varietal Denomination: Cutting Edge

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 14/999,229

(22) Filed: Apr. 12, 2016

(51) Int. Cl.
*A01H 5/02* (2006.01)

(52) U.S. Cl.
USPC ..... Plt./479

(58) Field of Classification Search
USPC ..... Plt./479
CPC ..... A01H 5/02
See application file for complete search history.

*Primary Examiner* — Kent L Bell

(57) ABSTRACT

A new, distinct *Sedum ellacombianum* plant as illustrated and described, characterized by yellow edged foliage, compared to the all green foliage of the parent plant.

1 Drawing Sheet

Latin name: *Sedum ellacombianum.*
Cultivar name: 'Cutting Edge'.

BACKGROUND OF THE INVENTION

The present invention relates to a new and distinct sport of *Sedum ellacombianum* plant named 'Cutting Edge' characterized by yellow edged foliage all growing season long, compared to the all green foliage of the parent plant. The new *Sedum ellacombianum* was found as a naturally occurring, whole plant sport of an unnamed *Sedum ellacombianum*, not patented, in Hebron, Ill. in 2013. The selection of the new plant was due to its' yellow edged foliage, compared to the green foliage of the parent plant. Initial asexual reproduction has taken place at a nursery in Hebron, Ill. since 2014 by means of division, and vegetative cuttings. The new *Sedum ellacombianum* has shown to be stable and identical in reproduction after rooting over 1000 plants from 2014 to 2015. No plants of the new *Sedum ellacombianum* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

The new *Sedum ellacombianum* plant named 'Cutting Edge' characterized by yellow edged foliage RHS color 151 A, April to October, compared to the green leaved parent plant have been observed to be unique and stable.

Plants of the new *Sedum ellacombianum* 'Cutting Edge' can be compared to plants of, the parent *Sedum ellacombianum* not patented. 1. The new *Sedum ellacombianum* plant has yellow edged foliage while the parent plant had all green foliage.

Plants of the new *Sedum ellacombianum* can be compared to plants of *Sedum ellacombianum* 'The Edge' not patented. 1. The new *Sedum ellacombianum* plant has yellow edged foliage RHS color 151 A that holds its color from April to October while *Sedum ellacombianum* 'The Edge' plant has a yellow edged foliage close to 150 A in April that turns almost green becoming much less noticeable by June.

Plants of the new *Sedum* can also be compared to *Sedum kamtschaticum* 'Variegatum', not patented. 1. The new *Sedum ellacombianum* plant has yellow edged foliage RHS color 151 A while *Sedum kamtschaticum* 'Variegatum' has yellow edged foliage colored RHS color 4 C. 2. The new *Sedum ellacombianum* plant has glossy foliage while *Sedum kamtschaticum* 'Variegatum' has matte foliage.

DESCRIPTION OF PHOTOGRAPHS

Figure 1:
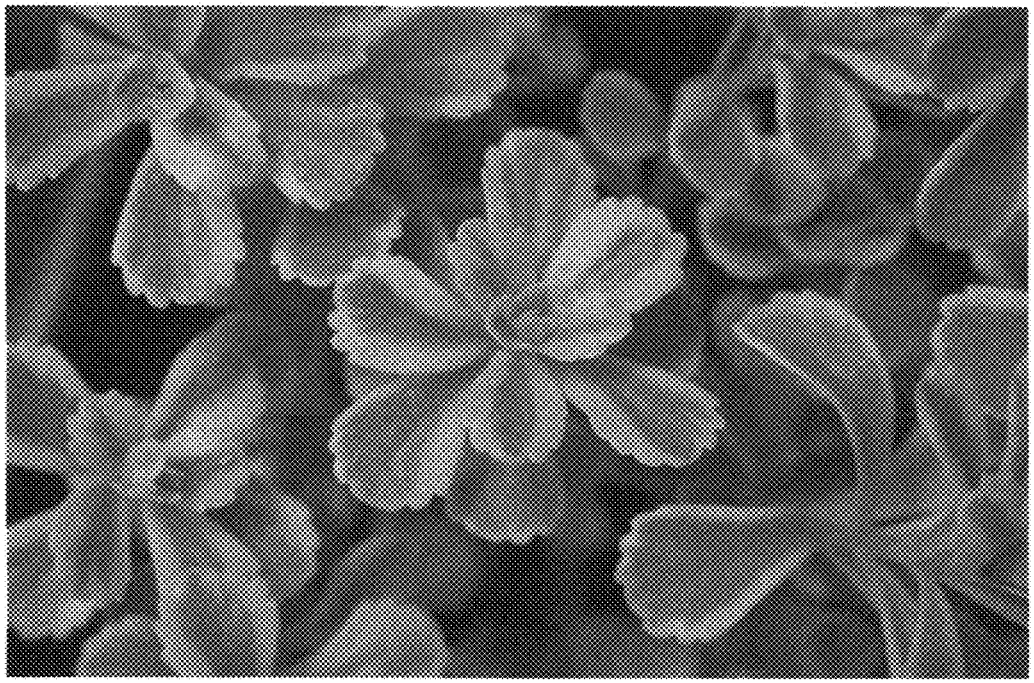
Figure 2:
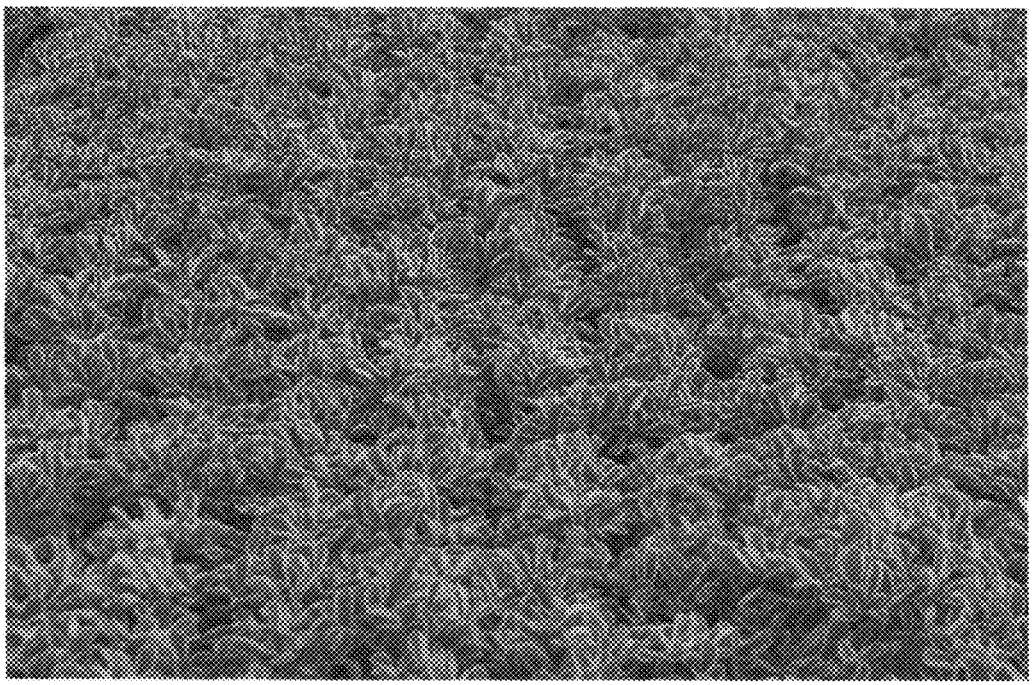

Plants pictured in the drawing were grown for one year.
FIG. 1. Close up of the foliage.
FIG. 2. A picture of many container plants together.

DETAILED BOTANICAL DESCRIPTION

In the following description, color references are made to The Royal Horticultural Society Colour Chart (2001). Plants used for the description were grown for one year. Measurements and numerical values represent averages of typical plants.

Botanical classification: *Sedum ellacombianum* cultivar Cutting Edge.

Parentage: A whole plant sport of an unnamed *Sedum ellacombianum.*

Propagation: Vegetative division and cutting propagation.

Plant description: Typical and observed plant habit of the new *Sedum ellacombianum* is basal clumps, reaching 30 cm wide with upright 15 cm tall stems topped by yellow flowers in June.

*Plant height.*—Average 15 cm.
*Plant width.*—30 cm.
*Stem color.*—199 D in spring, summer, and fall.
*Stem shape.*—Both typical and observed — round.
*Stem texture.*—Glabrous.
*Stem length.*—15 cm.
*Stem diameter.*—3 mm.
*Lateral branches.*—None observed.
*Internode length.*—5 cm.

Foliage:

*Type*.—Deciduous.
*Shape*.—Obovate.
*Petiole*.—None.
*Length*.—3 cm.
*Width*.—1 cm.
*Thickness*.—1-2 mm.
*Margin*.—Coarsely and irregularly toothed.
*Leaf apex, typical and observed*.—Obtuse.
*Leaf bases, typical and observed*.—Cuneate.
*Texture*.—Smooth.
*Leaf arrangement*.—Alternate, crowded except at the base of the stems.
*Leaf venation pattern*.—None noticed.
*Leaf vein color*.—None noticed.
*Adaxial leaf description*.—Color is 151 A at the variegated edge and close to 137 C in the center of the leaf.
*Abaxial leaf description*.—Color is 151 D at the variegated edge and close to 147 B in the center of the leaf.
*Fall foliage color*.—None noticed.

Flower:

*Petal count*.—5.
*Petal shape*.—Lanceolate.
*Adaxial petal color*.—12 A.
*Abaxial petal color*.—13 B.
*Petal apex shape*.—Acuminate.
*Petal base*.—2-3 mm wide.
*Petal length*.—6 mm.
*Petal width*.—2-3 mm.
*Petal texture*.—Typical and observed — glabrous.
*Petal margin, typical and observed*.—Entire.
*Petal bases, typical and observed*.—Obtuse.
*Inflorescence type*.—Panicle on basal flowering stems.
*Panicle color*.—12 A.
*Individual flower size*.—13 mm diameter, 6 mm depth.
*Flower shape*.—Stellate.
*Inflorescence length and width*.—3-4 cm across, 2 cm tall.
*Flower number*.—Approximately 50-60 per stem.
*Bloom period and duration*.—Early June to Early July.
*Flower longevity and duration on the plant*.—Approximately 3 weeks.
*Bud shape, typical and observed*.—Elliptical.
*Bud length, typical and observed*.—4 mm.
*Bud diameter, typical and observed*.—3 mm.
*Bud color, typical and observed*.—Close to 14 B.
*Sepal size*.—1 mm across, 3 mm length.
*Sepal number*.—5.
*Sepal shape, typical and observed*.—Narrow ovate.
*Sepal apex, typical and observed*.—Acute.
*Sepal margin, typical and observed*.—Entire.
*Sepal color, abaxial and adaxial typical and observed*.—Close to 145 B.
*Peduncle length, typical and observed*.—15 cm.
*Peduncle diameter, typical and observed*.—3 mm.
*Peduncle color, typical and observed*.—Close to 199 D.
*Peduncle texture, typical and observed*.—Glabrous.
*Pedicel length, typical and observed*.—6 mm.
*Pedicel diameter, typical and observed*.—1 mm.
*Pedicel color, typical and observed*.—Close to 199 D.
*Pedicel texture, typical and observed*.—Glabrous.
*Carpel color*.—14 B.
*Carpel surfaces*.—Glabrous.
*Stigma shape*.—Capitate.
*Stigma size*.—2 mm.
*Stigma color*.—13 A.
*Style length*.—1 mm.
*Style shape*.—Slender.
*Style color*.—12 A.
*Ovary size*.—1-2 mm.
*Ovary shape*.—Cordate.
*Ovary color*.—12 A.
*Pistil, typical and observed number*.—5, length 4-5 mm.
*Fertility*.—10 anthers, 10 stamens.
*Anther color*.—12 A, Pollen color — close to 17 B. Pollen amount — moderate.
*Anther shape*.—Ovate.
*Filament color*.—2 A.
*Blooming habit*.—Terminal panicle on up to 15 cm stems.
*Scent*.—No scent noticed.
*Fruit*.—None.
*Hardiness*.—U.S.D.A. hardiness zones 4-9.
*Disease resistance*.—Resistance to diseases common to *Sedum* has not been observed on plants grown under nursery conditions.
*Pest resistance*.—Resistance to pests common to *Sedum* has not been observed on plants grown under nursery conditions.

I claim:

1. A new, distinct *Sedum ellacombianum* plant as illustrated and described, characterized by yellow edged foliage, compared to the all green foliage of the parent plant.

* * * * *